(12) United States Patent
Suruga et al.

(10) Patent No.: US 9,301,985 B2
(45) Date of Patent: Apr. 5, 2016

(54) THERAPEUTIC AGENT FOR DEMENTIA

(71) Applicant: Kibun Foods Inc., Tokyo (JP)

(72) Inventors: Kohei Suruga, Tokyo (JP); Yasuhiro Komatsu, Saitama (JP); Kazunari Kadokura, Tokyo (JP); Yoshihiro Sekino, Kanagawa (JP); Kenichi Mishima, Fukuoka (JP); Michihiro Fujiwara, Fukuoka (JP)

(73) Assignee: KIBUN FOODS INC., Tokyo (JP)

( * ) Notice: Subject to any disclaimer, the term of this patent is extended or adjusted under 35 U.S.C. 154(b) by 382 days.

(21) Appl. No.: 13/798,633

(22) Filed: Mar. 13, 2013

(65) Prior Publication Data

US 2014/0271703 A1    Sep. 18, 2014

(51) Int. Cl.
*A61K 36/06* (2006.01)
*A61K 36/07* (2006.01)
*A61K 36/074* (2006.01)

(52) U.S. Cl.
CPC .............. *A61K 36/07* (2013.01); *A61K 36/074* (2013.01)

(58) Field of Classification Search
USPC .................................... 424/195.15
IPC .................................... A61K 36/06
See application file for complete search history.

(56) References Cited

U.S. PATENT DOCUMENTS

| | | | | |
|---|---|---|---|---|
| 7,442,541 | B2 * | 10/2008 | Tsubaki et al. | 435/254.1 |
| 7,977,379 | B2 * | 7/2011 | Kouge et al. | 514/459 |
| 2005/0276815 | A1 * | 12/2005 | Stamets | 424/195.15 |
| 2008/0081046 | A1 * | 4/2008 | Olalde | 424/195.15 |

FOREIGN PATENT DOCUMENTS

| | | | |
|---|---|---|---|
| JP | 2003002811 | * | 1/2003 |
| JP | 2007063206 | * | 3/2007 |
| JP | 2009027984 | * | 2/2009 |
| JP | 2010235463 | * | 10/2010 |
| KR | 2004035985 | * | 4/2004 |

OTHER PUBLICATIONS

Shimada, Atsushi et al "Erinacines E, F and G, Stimulators of Nerve Growth Factor (NGF)-Synthesis, from the Mycelia of Hericium erinaceum" Pergamon, Tetrahedron Letters, 37:41:7399-7402(1996).

Japanese Office Action, dated Mar. 17, 2015. Patent Application No. 2011-159770.

Ainsworth & Bisby's Dictionary of Fungi, Commonwealth Agricultural Bureaux Commonwealth Mycological Institute, Dec. 15, 2001, p. 224, 9th edition.

Hirokazu Kawagishi, Kinoko no. kinousei to sore wo tsukasadoru busshitsu (Functionality of mushrooms and substances regulating the same), Food Style 21, 2003, 70-73 vol. 7, No. 9.

Hirokazu Kawagishi, Kinoko ga tsukuridasu seitaichousetsukinoubusshitsu (Bioregulatory functional substances produced by mushrooms), Shokuhin to kaihatsu (Food and development), 2002, pp. 14-17, vol. 37, No. 3.

Hirokazu Kawagishi, Kinouseishokuhin to yakurieiyo (Functional foods and medical nutrition), J•JSMUFF, 2006, pp. 189-194, vol. 3, No. 3.

Saito, T. et al., Erinacine E as a kappa opioid receptor agonist and its new analogs from a basidiomycete, Hericium ramosum., J. Antibiot., 1998, pp. 983-990 vol. 51.

Office Action issued Jun. 9, 2015, in corresponding Japanese Patent Application No. 2011-159770, and English Excerption thereof.

\* cited by examiner

*Primary Examiner* — Chris R Tate
(74) *Attorney, Agent, or Firm* — Browdy and Neimark, PLLC

(57) ABSTRACT

The present invention provides a therapeutic agent for dementia comprising a pharmaceutically active substance derived from *Hericium ramosum*.

10 Claims, 2 Drawing Sheets

THERAPEUTIC AGENT FOR DEMENTIA

BACKGROUND OF THE INVENTION

1. Field of the Invention

This invention relates to a therapeutic agent for dementia, a method for producing the same, and a method for treating dementia. Specifically, it relates to a therapeutic agent for dementia derived from *Hericium ramosum*, a method for producing the same and a method for treating dementia using the therapeutic agent for dementia.

2. Description of the Related Art

In recent years, the society is further aging, and the rapid increase in the number of patients with dementia such as Alzheimer-type dementia or cerebrovascular dementia draws attention as a serious social problem. In particular, Alzheimer-type dementia is caused by the degeneration of nerve cells and is characterized by that its symptom proceeds gradually without patients' noticing. Further, because no fundamental therapeutic method has been established yet in the present medical science, the complete recovery is difficult once the disease is developed. Therefore, it is thought to be very important to reduce the risk of the degeneration of nerve cells by a certain active substance, in the stage before the progress of the disease situation or before the development of the disease, or to relief the symptom.

The research and development, such as the elucidation of the mechanism of pathogenesis of Alzheimer-type dementia or the search for a new medicine, are actively conducted. For example, in the brain of a patient with Alzheimer-type dementia, disorders such as the degeneration of neurofibril, the atrophy of nerve cells and the decrease in the nerve cell number are observed, and the pathology corresponds well with the disorder of basal forebrain cholinergic nerve cells, which relates to the memory and the learning ability. Since the nutritional factor for the basal forebrain cholinergic nerve cells is nerve growth factor (NGF), it is thought that the lack of NGF is one of the factors inducing Alzheimer-type dementia. Further, also regarding cerebrovascular dementia, the lack of NGF is thought to be one of the causes thereof.

Here, the neurotrophin family represented by nerve growth factor relates to the functional maintenance of nerve cells. It is thought that dementia such as Alzheimer's disease is caused, when they do not function normally. Since their nutritional factors are proteins, they cannot cross the blood-brain barrier (BBB) and thus cannot be administered orally or by injection. Therefore, it is considered effective for preventing and treating dementia to stimulate astroglia cells, which produce NGF and the like in the brain, to make them produce NGB in the brain.

Regarding a method for accelerating such NGF synthesis in the brain, a natural product of *Hericium erinaceum* (refer to non-patent document 1, which is expressly incorporated herein by reference in its entirety), which is an edible mushroom classified to *Hericiaceae, Hericium*, was found to include a hericenone and an erinacine which are the substances to accelerate the NGF synthesis (refer to non-patent document 2, which is expressly incorporated herein by reference in its entirety). Also because the case of *Hericium erinaceum* was the first case to find a substance which accelerates the NGF synthesis from a natural component except for an animal, the bioactive substances produced by *Hericium erinaceum* drew a lot of attention, and various studies have been conducted so far.

As an example, according to non-patent document 3, which is expressly incorporated herein by reference in its entirety, it is described that, in an animal experiment with a rat using hericenone C and erinacine A, which are the components derived from *Hericium erinaceum*, the apparent improvement of the memory retention and the learning ability was observed in the cerebrovascular dementia model, in which the vessel was artificially clogged, as well as in the Alzheimer's disease model.

Here, *Hericium ramosum* is known as an edible mushroom taxonomically close to *Hericium erinaceum*, and it is considered that only two species of *Hericium ramosum* and *Hericium erinaceum* belong to *Hericium*. While *Hericium erinaceum* has been known to bring a metabolic product thereof with a high specificity, *Hericium ramosum* has been well known to produce a totally different substance group from *Hericium erinaceum*, though they both belong to *Hericiaceae* (non-patent document 4, which is expressly incorporated herein by reference in its entirety). Therefore, *Hericium ramosum* has drawn little attention so far unlike *Hericium erinaceum*, and it has drawn little attention as a therapeutic agent for dementia.

Regarding the reports on the bioactive substances of *Hericium ramosum*, there were only a few examples such as a report that erinacine E derived from *Hericium ramosum* is an agonist for k-opioid receptor while erinacine E derived from *Hericium erinaceum* has an action to accelerate the nerve growth factor (NGF) production (non-patent document 5, which is expressly incorporated herein by reference in its entirety). That is, few examples which noticed the bioactive substances and functional components contained in *Hericium ramosum* have been known.

CITATION LIST

[Non-Patent Document 1] "Ainsworth & Bisby's Dictionary of Fungi" 9th edition, Commonwealth Agricultural Bureaux Commonwealth Mycological Institute, Dec. 15, 2001, p. 224

[Non-Patent Document 2] Hirokazu Kawagishi, "*Kinoko no kinousei to sore wo tsukasadoru busshitsu* (Functionality of mushrooms and substances regulating the same)", FOOD Style 21, 7(9), 70-73 (2003)

[Non-Patent Document 3] Hirokazu Kawagishi, "*Kinoko ga tsukuridasu seitaichousetsukinoubusshitsu* (Bioregulatory functional substances produced by mushrooms)", *Shokuhin to kaihatsu* (Food and development), 37(3), 14-17 (2002)

[Non-Patent Document 4] Hirokazu Kawagishi, "*Kinouseishokuhin to yakurieiyo* (Functional foods and medical nutrition)", J•JSMUFF, 3(3), 189-194 (2006)

[Non-Patent Document 5] Saito, T. et al., Erinacine E as a kappa opioid receptor agonist and its new analogs from a basidiomycete, *Hericium ramosum*., J. Antibiot., vol. 51, p. 983-990 (1998)

SUMMARY OF THE INVENTION

Under such a situation, when the present inventors examined the action to accelerate the NGF synthesis in the mouse brain in vivo using a freeze-dried product of a mycelium of *Hericium erinaceum*, it was found that the NGF production amount in hippocampus indeed increased. However, the actual situation is that the certain treatment and prevention of dementia have not been achieved, even in the case of using *Hericium erinaceum*. That is, the actual situation was that a substance having a higher NGF synthesis activity than conventional substances was desired, in view of making the treatment and prevention of dementia more efficient.

This invention was made in view of the above situations, and the problem that this invention is to solve is to provide a therapeutic agent for dementia which is excellent in the activity to accelerate the NGF synthesis.

The present inventors conducted extensive studies for the purpose of solving the above problems, examined the activity to accelerate the NGB synthesis in the mouse brain in vivo using a freeze-dried product of a mycelium of *Hericium ramosum*, and thus found that the NGF production amount was more than the case of using a freeze-dried product of a mycelium of *Hericium erinaceum*.

That is, this invention, which is the specific mean to solve the above problems, is as follows.

[1] A therapeutic agent for dementia comprising a pharmaceutically active substance derived from *Hericium ramosum*.
[2] The therapeutic agent for dementia according to [1], which is for oral administration.
[3] The therapeutic agent for dementia according to [1] or [2], wherein the active substance is derived from a mycelium of *Hericium ramosum*.
[4] The therapeutic agent for dementia according to [1] or [2], wherein the active substance is a freeze-dried product of a mycelium of *Hericium ramosum*.
[5] The therapeutic agent for dementia according to any one of [1] to [4], wherein the dementia is Alzheimer-type dementia or cerebrovascular dementia.
[6] A method for treating dementia comprising administering the therapeutic agent of any one of [1] to [5].
[7] A method for increasing nerve growth factor in hippocampus of a brain comprising administering an active substance derived from *Hericium ramosum* to a mammal.
[8] The method according to [7], wherein the active substance is administered orally.
[9] The method according to [7] or [8], wherein the mammal is a human.
[10] A method for producing a therapeutic agent for dementia comprising freeze-drying *Hericium ramosum*.

According to this invention, a therapeutic agent for dementia excellent in the activity to accelerate the NGF synthesis can be provided.

BEST MODE FOR CARRYING OUT THE INVENTION

Figure 1:
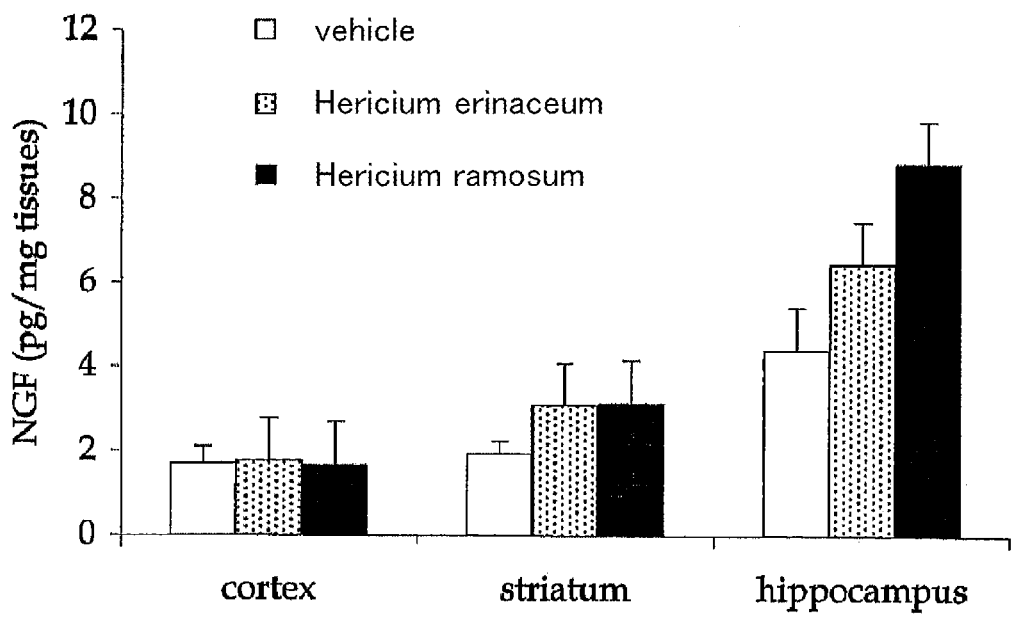
FIG. 1 is a graph of the results for the comparison experiment of the activities to accelerate the NGF synthesis between the mycelium of *Hericium ramosum* and the mycelium of *Hericium erinaceum*.

The therapeutic agent for dementia of this invention is explained in detail below.

The explanations for the constituent features described below are sometimes made based on the representative embodiments of this invention, but this invention is not restricted by such embodiments. In this connection, the numeral range represented using "-" in this specification means the range including the values described before and after "-" as the lower limit and the upper limit.

[Therapeutic Agent for Dementia]

The therapeutic agent for dementia of this invention is characterized by including an active substance (an active component) derived from *Hericium ramosum*.

The therapeutic agent for dementia of this invention is explained below. In this regard, in this specification, the term therapeutic agent for dementia is sometimes used as a term to represent the concept including the preventive agent.

(Active Substance)

The above active substance is not particularly restricted as long as it is derived from *Hericium ramosum*. *Hericium ramosum* can be used in both states of a fruit body and a mycelium, but it is preferable to use a cultured mycelium in order to keep a uniform quality and standard and to stabilize and uniformize. That is, regarding the therapeutic agent for dementia of this invention, it is preferable that the active substance derived from *Hericium ramosum* is derived from the mycelium of *Hericium ramosum*.

In this invention, the fruit body is a structure that a germ forms from a mycelium for the spore formation, and refers to the general edible structure of a mushroom. On the other hand, the mycelium is an aggregate of mycelia formed through the budding of the spore and the repetitive cell division.

(Action of Active Substance)

The therapeutic agent for dementia of this invention has an action to accelerate (induce) the NGF production. Thus, it is useful as a therapeutic medicine or a preventive medicine for Alzheimer-type dementia, and a therapeutic medicine or a preventive medicine for (cerebro)vascular dementia which is early-onset dementia except for Alzheimer-type (dementia associated with the aftereffect of cerebral infarction). In addition to these actions, it is also preferable that the actions to improve the space recognition and learning ability and improve the memory and the like are included.

The therapeutic agent for dementia of this invention can increase nerve growth factor in hippocampus of a brain of a sample animal by administering the active substance derived from *Hericium ramosum* to the sample animal. Further, the therapeutic agent for dementia of this invention can increase nerve growth factor (NGF) in hippocampus of a brain of a sample animal by preferably making the active substance derived from *Hericium ramosum* to be orally ingested. Here, the method for measuring NGF in the brain is not particularly restricted, but the amount of nerve growth factor in each brain tissue can be measured by extirpating by a surgical method and using enzyme-linked immunosorbent assay (ELISA) or NGF E max Immuno Assay System.

Such a therapeutic agent for dementia of this invention has the above actions, in particular when the above sample animal is a mammal. The mammal includes a human, and the therapeutic agent for dementia of this invention can be preferably administered to a human.

Furthermore, the above active substance derived from *Hericium ramosum* used for the therapeutic agent for dementia of this invention has preferably an antioxidant activity.

In this connection, the therapeutic agent for dementia of this invention may improve other brain functions, and for example, the tranquilizing action, the inhibition of the frustrated feeling and the palpitation, the enhancement of the relaxed feeling, the prevention of the accumulation of stress, the generation of a wave and the like are mentioned.

(Form)

The therapeutic agent for dementia of this invention can be used as a pharmaceutical, a supplement food or a general food, after being made into a composition added with a general additive component. As the additive component, for example, a conventionally used pharmaceutically acceptable additive such as a surfactant, a solvent, a thickener, a stabilizer, a preservative, an antioxidant, a flavor or the like, another component or compound having the activity to accelerate the NGF production, a component d or a compound having another functionality (an effect of improving the blood flow, an effect of inhibiting the hypertension or the like), or the like are mentioned.

As the form of the therapeutic agent for dementia of this invention, a powder, a tablet, a capsule, a gelatin agent, a paste or a troche, a gum, or a solution, a dispersion liquid or an emulsion which are drinkable (hereinbelow, these are referred to a medicinal solution as a whole) and the like are mentioned, but the form is not restricted to these. Further, these forms can be produced by the conventionally known methods.

Among them, the therapeutic agent for dementia of this invention is preferably a powder or a medicinal solution. That is, it is preferable that *Hericium ramosum* is made into a powder by an arbitrary method, or *Hericium ramosum* is made into a medicinal solution using an arbitrary vehicle. Further, the therapeutic agent for dementia of this invention is more preferably a medicinal solution. In this connection, the vehicle is not particularly restricted, and those conventionally known in the field, to which this invention belongs, can be used.

[Method for Producing Therapeutic Agent for Dementia]

The method for preparing the active substance from *Hericium ramosum* is not particularly restricted, and a living body of *Hericium ramosum* can be used or a dried product can be also used. Further, the active substance can be extracted from *Hericium ramosum* by a known method. Furthermore, the active substance extracted can be purified by a general method. In this invention, it is preferable to use the dried product of *Hericium ramosum*.

When the therapeutic agent for dementia in a powder form is prepared, it is preferable to pulverize freeze-dried *Hericium ramosum* to make a powder. On the other hand, when the therapeutic agent for dementia in a medical solution form is prepared, it is preferable to prepare an aqueous solution or an aqueous dispersion from *Hericium ramosum* using water as a vehicle, and it is more preferable to make a freeze-dried product of *Hericium ramosum* into an aqueous solution or an aqueous dispersion at this timing. However, another liquid or a general additive component can be added to the medicinal solution, and another arbitrary active component of a therapeutic agent for dementia can be added, as long as it is not inconsistent with the purpose of this invention.

In this regard, the active substance in the therapeutic agent for dementia of this invention may be water-soluble, water-insoluble or lipid-soluble. Further, more than one active substances can be included, and, in such a case, for example, a water-soluble component and a lipid-soluble component can be included. When the therapeutic agent for dementia of this invention is made into an aqueous dispersion, in particular, it can be prepared by using a certain fraction of the aqueous dispersion after the separation or purification, but it is preferable to use the whole aqueous dispersion of *Hericium ramosum*.

In addition, the active substance derived from *Hericium ramosum* in the therapeutic agent for dementia of this invention is preferably one derived from a freeze-dried product of a mycelium of *Hericium ramosum*, and is more preferably a freeze-dried product of a mycelium of *Hericium ramosum*. That is, the method for producing the therapeutic agent for dementia of this invention preferably includes a step of freeze-drying *Hericium ramosum*.

In this regard, there is no particular restriction to the method for freeze-drying. Further, a component in *Hericium ramosum* before freeze-drying can be used as the active substance after being changed through a step of freeze-drying, or a component in *Hericium ramosum* before freeze-drying as it is can be used as the active substance without being changed through a step of freeze-drying.

[Method for Treating Dementia]

(Method for Administering)

Furthermore, the therapeutic agent for dementia of this invention can cross the blood-brain barrier as demonstrated in Examples of this invention, and can increase the NGF production amount in hippocampus of the mouse brain in vivo. Accordingly, it is supposed to be a substance to accelerate the NGF synthesis, although we are not particular about any theory.

Therefore, it is not necessary to administer the therapeutic agent for dementia of this invention locally, and the injection administration and the oral administration are possible.

The therapeutic agent for dementia of this invention is more preferably an oral therapeutic agent, from the viewpoint of using easily as a therapeutic agent for dementia.

Further, since the therapeutic agent for dementia of this invention is derived from edible *Hericium ramosum*, it is thought to be highly safe and can be taken every day. Thus, the active substance included in the therapeutic agent for dementia of this invention can be used not only as a therapeutic agent for improving the symptom of dementia, but also as a preventive agent for dementia which can be taken constantly.

Regarding the therapeutic agent for dementia of this invention, there is no particular restriction to the dose of the active substance per 1 kg of body weight of the sample animal, and it can differ according to the age, body weight and the like of the sample animal (subject) which ingests the agent. For example, it is preferably 5 mg/kg or more, more preferably 5-25 mg/kg, and particularly preferably 25-30 mg/kg.

There is no particular restriction to the number of doses of the therapeutic agent for dementia of this invention, but, for example, it can be administered 1 time a day to 4 times a day, it is preferable to administer 2-4 times a day and it is preferable to administer 1 time a day.

Further, there is no particular restriction to the administration interval, either, but, for example, it is preferable to administer every 6-8 hours, and it is preferable to administer one time per 12-36 hours.

In addition, there is no particular restriction to the period for administration, either, but, for example, it is preferably two weeks or more, and more preferably 2-16 weeks. In this regard, it is known that the NGF production amount can be increased, when it is administered for two weeks, for example.

(Preparation Method)

The therapeutic agent for dementia of this invention can be prepared according to a known method. The concentration of the active substance when used as a medicinal solution can be adjusted within the range in which the effects of this invention are achieved.

EXAMPLES

The features of this invention are explained in detail below with reference to Examples.

The materials, amounts, proportions, contents of the treatment, procedures of the treatment and the like shown in Examples below can be appropriately changed as long as it does not defeat the purpose of this invention. Thus, the scope of this invention should not be interpreted restrictively by the specific examples shown below.

Example 1

Comparison of Activities to Accelerate NGF Synthesis Between Mycelium of *Hericium ramosum* and Mycelium of *Hericium erinaceum*

A freeze-dried product of a mycelium of *Hericium ramosum* and a freeze-dried product of a mycelium of *Hericium erinaceum* were prepared according to an ordinal method.

Using the sample of each freeze-dried product prepared above, a medicinal solution having a concentration of 300 mg/kg was prepared. In this regard, an aqueous dispersion was prepared using deionized water as the vehicle of the medicinal solution. Here, although each freeze-dried product did not completely dissolve in water, it is thought that a part of the water-soluble components was dissolved in water.

Each medicinal solution obtained was orally administered for two weeks once a day with a dose of 0.2 ml per 10 g of body weight of a mouse. At this point, 10 7-week-old healthy mice were used for each medicinal solution.

From the mice, to which each medicinal solution was administered for two weeks, the cortex, striatum and hippocampus, which are the nerve nuclei in the brain, were each extracted, and the amount of nerve growth factor (NGF) in each brain tissue was measured using enzyme-linked immunosorbent assay (ELISA).

The results obtained are shown in FIG. 1. In this regard, in FIG. 1, the graphs for each brain tissue represent the amounts of NGF in the cases of the administration of the vehicle only, the administration of the freeze-dried product of the mycelium of *Hericium erinaceum*, and the administration of the freeze-dried product of the mycelium of *Hericium ramosum*, respectively starting from the left.

From FIG. 1, it was shown regarding hippocampus that the increased amount of the NGF production amount of the medicinal solution-administration relative to the administration of the vehicle only was twice as much in the mice administered with the medicinal solution, that was the therapeutic agent for dementia of this invention using the freeze-dried product of the mycelium of *Hericium ramosum*, as the mice administered with the medicinal solution using the freeze-dried product of the mycelium of *Hericium erinaceum*.

Further, also regarding striatum, the increase in the NGF production amount was shown in the case of administration of the medicinal solution that was the therapeutic agent for dementia of this invention using the freeze-dried product of the mycelium of *Hericium ramosum*, as compared with the administration of the vehicle only. In addition, regarding the increase in the NGF production amount in striatum, the medicinal solution that is the therapeutic agent for dementia of this invention using the freeze-dried product of the mycelium of *Hericium ramosum* was comparable with the medicinal solution using the freeze-dried product of the mycelium of *Hericium erinaceum*.

Example 2

Amount Dependence Experiment for Activity to Accelerate NGF Synthesis of Mycelium of *Hericium ramosum*

Medicinal solutions were prepared using the freeze-dried product of the mycelium of *Hericium ramosum* similarly to Example 1, except that the concentrations per 1 kg of the medicinal solution were changed to 100 mg (100 mg/kg), 300 mg (300 mg/kg; the same concentration as in Example 1) and 600 mg (600 mg/kg).

Each medicinal solution obtained was orally administered for two weeks once a day with a dose of 0.2 ml per 10 g of body weight of a mouse as in Example 1. At this point, 10 7-week-old healthy mice were used for each medicinal solution.

Hippocampus was each extracted from the mice, to which each medicinal solution was administered for two weeks, and the amount of nerve growth factor (NGF) in each brain tissue was measured using enzyme-linked immunosorbent assay (ELISA).

Figure 2:
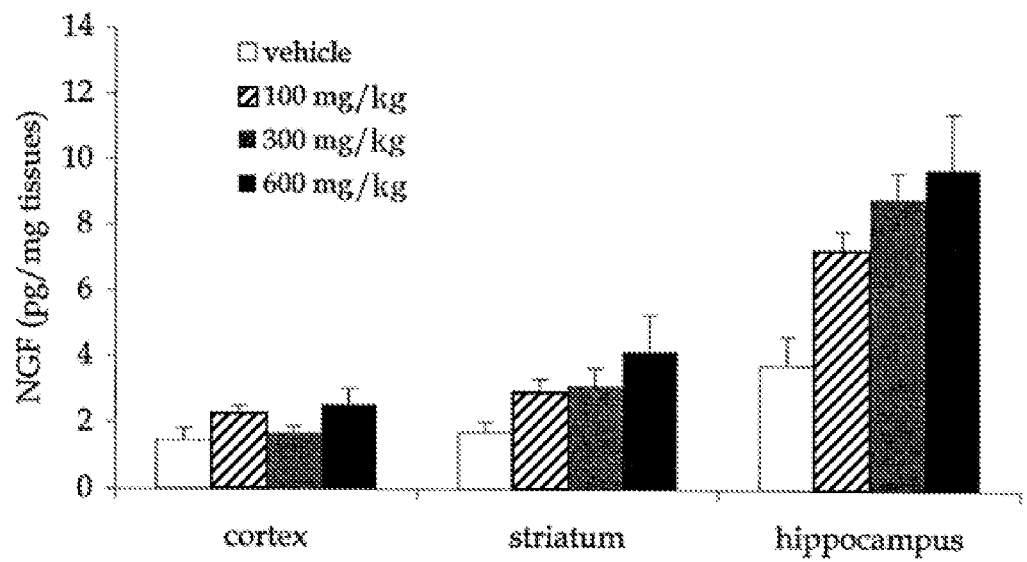
FIG. 2 is a graph of the results for the amount dependence experiment for the activity to accelerate the NGF synthesis of the mycelium of *Hericium ramosum*.

The results obtained are shown in FIG. 2. In this regard, in FIG. 2, the graphs for each brain tissue represent the amounts of NGF in the cases of the administration of the vehicle only, the administration of the freeze-dried product of the mycelium of *Hericium ramosum* at 100 mg/kg, the administration of the freeze-dried product of the mycelium of *Hericium ramosum* at 300 mg/kg, and the administration of the freeze-dried product of the mycelium of *Hericium ramosum* at 600 mg/kg, respectively starting from the left.

From FIG. 2, it was found that the increased amount of the NGF production amount of the medicinal solution-administration in comparison with the administration of the vehicle only increased depending on the concentration of the medicinal solution using the freeze-dried product of the mycelium of *Hericium ramosum* (namely the amount of the freeze-dried product of mycelium of *Hericium ramosum*).

As shown in the results of Example 1 and Example 2 above, in comparison with the administration of the vehicle only, the group administered with the therapeutic agent for dementia derived from the mycelium of *Hericium ramosum* of this invention showed the tendency towards the increase in the NGF amounts in all the nerve nuclei. In particular, it was found that the increased amount of the NGF amount in hippocampus was large, and that the increased amount was twice as much as that of the case of using the mycelium of *Hericium erinaceum* which was conventionally known. That is, it was found that the therapeutic agent for dementia of this invention using the freeze-dried product of the mycelium of *Hericium ramosum* can increase the NGF production amount especially in hippocampus, and that it is thus useful as a therapeutic medicine or a preventive medicine for Alzheimer-type dementia, or a therapeutic medicine or a preventive medicine for (cerebro)vascular dementia which is early-onset dementia except for Alzheimer-type (dementia associated with the aftereffect of cerebral infarction).

Example 3

Antioxidant Activity of Mycelium of *Hericium ramosum*

Figure 3:
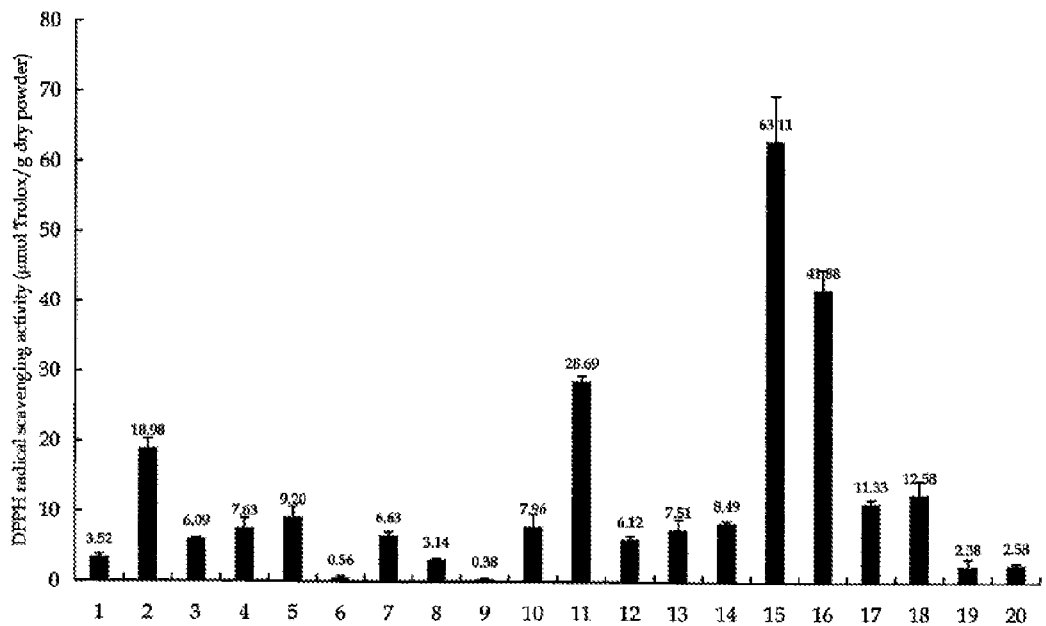
FIG. 3 is a graph of the results for the comparison experiment of the antioxidant activities of various mushroom mycelia.

Antioxidant activities (DPPH radical scavenging activities) of mycelia of various mushrooms were measured in vitro. In this regard, a freeze-dried product of the mycelium of each mushroom was made into a powder and was used. The production amount (μmol) of trolox (6-hydroxy-2,5,7,8-tetramethyl-chroman-2-carboxylic acid) per 1 g of each powder, which is a general index for antioxidant activity, was measured. The results are shown in FIG. 3. Regarding the abscissa in FIG. 3; 1 indicates *Sarcomixa serotina*; 2 indicates *Lyophyllum shimeji*; 3 indicates *Lepista nuda*; 4 indicates *Hypsizigus ulmarius*; 5 indicates *Pholiota nameko*; 6 indicates *Pholiota aurivella*; 7 indicates *Sparassis crispa*; 8 indicates

*Polyporus tuberaster*; 9 indicates *Polyporus badius*; 10 indicates *Laetiporus sulphureus*; 11 indicates *Grifola frondosa*; 12 indicates *Polyporus umbellatus*; 13 indicates *Lentinula edodes*; 14 indicates *Inonotus obliquus* (Chaga); 15 indicates *Hericium ramosum*; 16 indicates *Hericium erinaceum*; 17 indicates *Ganoderma lucidum* (Reishi); 18 indicates *Elfvingia applanata*; 19 indicates *Mycoleptodonoides aitchisonii*; and 20 indicates *Agaricus subrufescens*.

From FIG. 3, it was found that *Hericium ramosum* (15) has the largest antioxidant activity among them, and has a higher antioxidant activity than *Hericium erinaceum* (16) especially.

As shown in Example 3 above, the therapeutic agent for dementia of this invention including the active substance derived from *Hericium ramosum* has indeed a high antioxidant activity, and thus is expected to be able to remove the reactive oxygen efficiently. The reactive oxygen (free radical) in the brain is now expected to be one of the causes for the onset of dementia, and thus, such a therapeutic agent for dementia of this invention was found to be useful as a preventive agent for dementia from such a viewpoint.

Example 4

Total Polyphenol Amount of Mycelium of *Hericium ramosum*

Figure 4:
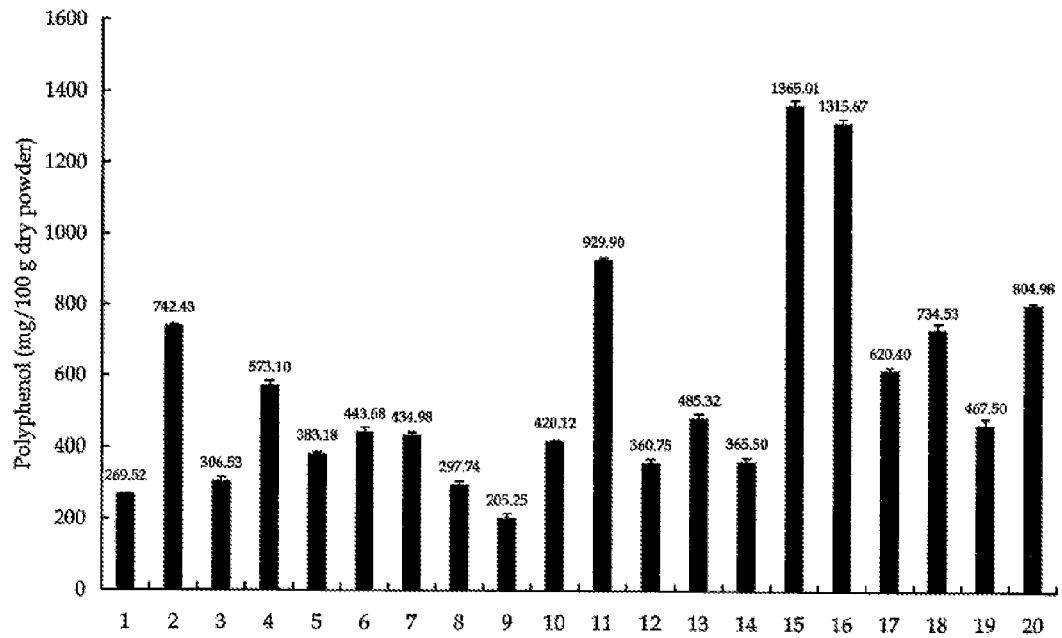
FIG. 4 is a graph of the results for the comparison experiment of the total polyphenol amounts of various mushroom mycelia.

The total polyphenol amounts of various mushroom mycelia were measured in vitro. In this regard, a freeze-dried product of each mushroom mycelium was made into a powder and was used. The total polyphenol amount per 100 g of each powder was measured. The results are shown in FIG. 4. The abscissa of FIG. 4 is the same as the abscissa of FIG. 3.

From FIG. 4, it was found that *Hericium ramosum* (15) has the largest total polyphenol amount among them, and has a larger amount to some extent than that of *Hericium erinaceum* (16) although the amount is comparable with that of *Hericium erinaceum* (16) especially.

There are some known reports that a polyphenol, which is one of the antioxidant substances, can inhibit the expression of apoE4 gene, which is predicted to be a gene to cause Alzheimer's disease, or can reduce the possibility to cause Alzheimer's disease by actually ingesting continuously. As in Example 4 above, the therapeutic agent for dementia of this invention having a high total polyphenol amount was found to be useful as a preventive agent for Alzheimer's disease also from such a viewpoint.

While the present invention has been described in detail and with reference to specific embodiments thereof, it will be apparent to one skilled in the art that various changes and modifications can be made therein without departing from the spirit and scope thereof.

The present disclosure relates to the subject matter contained in Japanese Patent Unexamined Publication No. 2013-23472, the contents of which are expressly incorporated herein by reference in their entirety. All the publications referred to in the present specification are also expressly incorporated herein by reference in their entirety.

The foregoing description of preferred embodiments of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention not be limited by the specification, but be defined claims set forth below.

What is claimed is:

1. A method for treating dementia, comprising administering to a mammal in need thereof a pharmaceutically effective amount of freeze-dried *Hericium ramosum* mycelia, wherein the freeze-dried mycelia contain a mixture of active substances.

2. The method according to claim 1, wherein the active substances have an antioxidant activity.

3. The method according to claim 2, wherein the active substances include a polyphenol.

4. The method according to claim 1, wherein the active substances include a polyphenol.

5. A method for increasing nerve growth factor in the hippocampus of a brain, comprising administering to a mammal in need thereof a pharmaceutically effective amount of freeze-dried *Hericium ramosum* mycelia, wherein the freeze-dried mycelia contain a mixture of active substances.

6. The method according to claim 5, wherein the freeze-dried *Hericium ramosum* mycelia is administered orally.

7. The method according to claim 5, wherein the mammal is a human.

8. The method according to claim 5, wherein the active substances have an antioxidant activity.

9. The method according to claim 8, wherein the active substances include a polyphenol.

10. The method according to claim 5, wherein the active substances include a polyphenol.

* * * * *